United States Patent
Shi et al.

(10) Patent No.: US 9,574,227 B2
(45) Date of Patent: Feb. 21, 2017

(54) METHOD FOR DETECTING VARIATION OF GENE FOR NON-DIAGNOSTIC PURPOSE BASED ON FLUORESCENCE QUENCHING AND PROBE THEREOF

(71) Applicant: SHANGHAI QY BIOTECH CO., LTD., Shanghai (CN)

(72) Inventors: Rui Shi, Shanghai (CN); Bochun Huang, Shanghai (CN)

(73) Assignee: SHANGHAI QY BIOTECH CP., LTD., Shanghai (CN)

( * ) Notice: Subject to any disclaimer, the term of this patent is extended or adjusted under 35 U.S.C. 154(b) by 124 days.

(21) Appl. No.: 14/352,438

(22) PCT Filed: Oct. 17, 2012

(86) PCT No.: PCT/CN2012/083104
§ 371 (c)(1),
(2) Date: Apr. 17, 2014

(87) PCT Pub. No.: WO2013/056651
PCT Pub. Date: Apr. 25, 2013

(65) Prior Publication Data
US 2014/0272978 A1    Sep. 18, 2014

(30) Foreign Application Priority Data
Oct. 19, 2011   (CN) .......................... 2011 1 0318975

(51) Int. Cl.
C07H 21/04    (2006.01)
C12Q 1/68     (2006.01)

(52) U.S. Cl.
CPC .......... *C12Q 1/6818* (2013.01); *C12Q 1/6869* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 5,945,283 | A * | 8/1999 | Kwok .................. | C12Q 1/6818 435/6.12 |
| 2006/0223064 | A1* | 10/2006 | Rudi ................... | C12Q 1/6818 435/6.14 |
| 2009/0209434 | A1* | 8/2009 | Shafer ................. | C12Q 1/6818 506/9 |
| 2010/0255482 | A1* | 10/2010 | Shen .................... | C12Q 1/6883 435/5 |

OTHER PUBLICATIONS

Rudi et al (BioTechniques 40 (3), 323 (2006)).*

* cited by examiner

*Primary Examiner* — James Martinell (57) ABSTRACT

A method for detecting variation of gene based on fluorescence quenching quantification comprises: performing single base extension at a specific site of a gene to be detected with marked probes and marked dideoxyribonucleotide triphosphate; detecting fluorescence quenching values, and determining SNP of the gene to be detected. The present invention also provides an oligonucleotide probe for the method.

2 Claims, 13 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 1
caaggtgaat ggtgagcaga                                            20

<210> SEQ ID NO 2
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 2
agagacacga cggtgagagg                                            20

<210> SEQ ID NO 3
<211> LENGTH: 39
<212> TYPE: DNA
<213> ORGANISM: Artificial sequence
<220> FEATURE:
<221> NAME/KEY: misc_feature
<223> OTHER INFORMATION: Probe

<400> SEQUENCE: 3
aaaaaaaaac accaggctct acagtaatga ctttaactc                       39

<210> SEQ ID NO 4
<211> LENGTH: 20
<212> TYPE: DNA
<213> ORGANISM: Artificial sequence
<220> FEATURE:
```

```
<221> NAME/KEY: misc_feature
<223> OTHER INFORMATION: Primer

<400> SEQUENCE: 4
gggcctactg tggctactca                                            20

<210> SEQ ID NO 5
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 5 cccttttcc aggtctgaca                                             20

<210> SEQ ID NO 6
<211> LENGTH: 25
<212> TYPE: DNA
<213> ORGANISM: Artificial sequence
<220> FEATURE:
<221> NAME/KEY: misc_feature
<223> OTHER INFORMATION: Probe

<400> SEQUENCE: 6
tcaggcatgc acaccttgtc cttca                                      25

<210> SEQ ID NO 7
<211> LENGTH: 26
<212> TYPE: DNA
<213> ORGANISM: Artificial sequence
<220> FEATURE:
<221> NAME/KEY: misc_feature
<223> OTHER INFORMATION: Probe

<400> SEQUENCE: 7
tcaggcatgc acaccttgtc cttcac                                     26

<210> SEQ ID NO 8
<211> LENGTH: 26
<212> TYPE: DNA
<213> ORGANISM: Artificial sequence
<220> FEATURE:
<221> NAME/KEY: misc_feature
<223> OTHER INFORMATION: Probe

<400> SEQUENCE: 8
tcaggcatgc acaccttgtc cttcat                                     26
```

METHOD FOR DETECTING VARIATION OF GENE FOR NON-DIAGNOSTIC PURPOSE BASED ON FLUORESCENCE QUENCHING AND PROBE THEREOF

CROSS REFERENCE OF RELATED APPLICATION

This is a U.S. National Stage under 35 U.S.C 371 of the International Application PCT/CN2012/083104, filed Oct. 17, 2012, which claims priority under 35 U.S.C. 119(a-d) to CN 201110318975.5, filed Oct. 19, 2011.

BACKGROUND OF THE PRESENT INVENTION

Field of Invention

The present invention relates to a technical field of nucleic acid test, and more particularly to a method for detecting SNP (single nucleotide polymorphism) for non-diagnostic purpose and a detecting probe therefor.

Description of Related Arts

The genetic science is an important field in biological science. Genetic sequence with code of human and also its variation will affect various biological functions of human and cause functional discord. The functional discord of human could be known and predicted by detecting SNPs of human Nowadays, SNP detection has become important for analyzing and diagnosing genetic diseases and drug reactions of individualized medicine. The SNP detection is also an important method for predicting and preventing many diseases, for example, determining risks of endocrine diseases including diabetes, and various cancers.

Nowadays, main methods for detecting SNP are Sanger's sequencing and method with Taqman probe. The Sanger's sequencing requires expensive sequencers, so that detecting cost is high. In addition, the sequencer is complicated to operate and maintain, and thus has not been equipped in hospitals and R&D institutions in most cities. Shortages of the method with Taqman probe are as follows. 1) It is difficult to design the probes, and usually a pair of suitable probes is selected at last after screening many times. What's more, the screening often fails. 2) It requires two probes to detect one SNP, so that the cost is high. 3) The method with Taqman probe is not site-specific, and thus the method has lower sensitivity and specificity for detecting single-base mutation; which usually causes false negative or false positive.

SUMMARY OF THE PRESENT INVENTION

An object of the present invention is to provide a method for detecting variation of gene for non-diagnostic purpose based on fluorescence quenching, which is simple, convenient and efficient, and has low cost, high specificity and high sensitivity.

In order to accomplish the above object, a method for detecting variation of gene for non-diagnostic purpose based on fluorescence quenching comprises following steps of:

1) extracting DNA from a sample;
2) amplifying a gene segment to be detected based on the DNA;
3) performing an extension reaction with product of the step 2) as a template, probes, and ddNTP (dideoxyribonucleotide triphosphate), and performing a fluorescence quenching reaction at the same time; wherein the probe is marked with quenching molecules, and the ddNTP is marked with fluorescent molecules; alternatively, the probe is marked with a fluorescence molecule, and the ddNTP is marked with a quenching molecule;
4) detecting changes of fluorescence caused by the extension reaction in the step 3), and calculating fluorescence quenching values; and
5) determining SNP of gene to be detected according to calculating results in the step 4).

Preferably, a distance between the fluorescence molecule or the quenching molecule and 3' end of the probe marked with the fluorescence molecule or the quenching molecule is 3-35 bp.

Preferably, the quenching molecule is BHQ1, BHQ2, BHQ3, TAMRA, Dabcyl or Eclipse, and the fluorescence molecule is fluorescein, R6G Cy3, Cy5, FAM or VIC.

Preferably, a number for cycles of the extension reaction in the step 3) is 35-40.

Preferably, the step 4) further comprises a step of correcting the fluorescence quenching value, wherein the fluorescence quenching value is corrected by being compared with an external standard control group in which the fluorescence attenuates naturally.

Another object of the present invention is to provide an oligonucleotide probe for the above method.

In order to accomplish the above object, the oligonucleotide probe in the present invention comprises at least one probe, for example, a single probe, double probes. Each probe is an oligonucleotide sequence comprising 15-45 nucleotides and marked with the fluorescence molecule or the quenching molecule. The distance between the fluorescence molecule or the quenching molecule and 3' end of the oligonucleotide sequence marked with the fluorescence molecule or the quenching molecule is 3-35 bp.

In the method for detecting variation of gene of the present invention, a type of a base extending at 3' end of the probe was determined by the fluorescence quenching reaction, in order to determine a type of a base at a specific site of the gene to be detected. Compared with Sanger's sequencing, the method in the present invention not only significantly saves time and cost of detection, but also avoids false positive caused by excessive amplification. Compared with the method with Taqman probe, the method in the present invention has higher specificity and sensitivity for detecting SNPs. In addition, a detecting platform in the present invention is embodied as a real-time fluorescent quantitative PCR instrument, or a common PCR instrument and a fluorescence enzyme-labeling instrument. Therefore, the method could be popularized in various hospitals and scientific research institutions.

These and other objectives, features, and advantages of the present invention will become apparent from the following detailed description, the accompanying drawings, and the appended claims.

DETAILED DESCRIPTION OF THE PREFERRED EMBODIMENT

The present invention is further described in detail as follows, according to drawings and embodiments.

The following examples are only for illustrating the present invention, but not for limiting the scope of the present invention. Experimental methods without specific conditions in the examples are conducted under routine conditions, such as conditions recited in Sambrook et al., *Molecular clone: Laboratory manual* (New York: Cold Spring Harbor Laboratory Press, 1989), and conditions advised by manufacturer.

Example 1

SNP Detection of 5HT2A Gene (1) Extracting DNA from a Sample

A proper amount of human oral mucosal epithelial cells were taken, which were provided by volunteers, and DNA was extracted from the human oral mucosal epithelial cells.

(2) PCR Amplification

Based on the DNA extracted, a 5HT2A gene segment in the DNA was amplified by PCR.

Sequences of primers used in the PCR were as follows.

```
                                            (SEQ ID NO: 1)
Forward primer: CAAGGTGAATGGTGAGCAGA (SEQ ID NO: 2)
Reverse primer: AGAGACACGACGGTGAGAGG
```

The primers recited above were provided by Shanghai Sangon Biological Engineering Co. Ltd.

A system of the PCR was as follows. 10×PCR buffer 1.5 µL, 25 mM $Mg^{2+}$ 1.2 µL, 10 mM dNTP 0.3 µL, Betaine 2 µL, DNA template 1 µL, 5 µM forward primer 1 µL, 5 µM reverse primer 1 µL, 5 U/µL rTaq 0.1 µL, $H_2O$ 6.9 µL, total volume 15 µL Conditions of the PCR were shown in Table 1.

TABLE 1

| Conditions of PCR | | |
|---|---|---|
| Reaction temperature | Reaction time | Cycle number |
| 95° C. | 5 minutes | |
| 95° C. | 30 seconds | 15 |
| 65~50° C. (decreasing by 1° C. per cycle) | 30 seconds | |
| 72° C. | 45 seconds | |
| 95° C. | 30 seconds | 20 |
| 50° C. | 30 seconds | |
| 72° C. | 45 seconds | |
| 4° C. | ∞ | |

(3) Purification of PCR Products

Product of the PCR was collected and then purified.

A system of purifying reaction was as follows. PCR product 15 µL, 5U/µL SAP 1 µL, 5 U/µL exonuclease I (Exo I) 1 µL, total volume 17 µL Conditions of the purifying reaction were as follows. 37° C., 30 minutes; 85° C., 15 minutes (4) Extension Reaction and Quenching Reaction On a real-time fluorescent quantitative PCR instrument (ABI 7900HT), a proper amount of the product of the PCR which had been purified was used as a template to perform an extension reaction with probes carrying quenching molecules and ddNTP (dideoxyribonucleotide triphosphate) marked with fluorescent molecules, and then oligonucleotide carrying fluorescence was obtained; meanwhile, a fluorescence quenching reaction was performed; wherein three experiments were conducted in parallel; an external standard control group and a blank control group were set; and fluorescence attenuated naturally in the external standard control group which was for correcting fluorescence quenching values of experimental groups.

A sequence of the probe in the example 1 was as follows.

```
                                                    (SEQ ID NO: 3)
5'-AAAAAAAAACACCAGGCTCTACAGTAAT(BHQ1)GACTTTAACTC-3'
```

The probe was synthesized by Shuoshi Biological Technology co. Ltd.

A system of the extension reaction was as follows. 10× Therminator DNA Polymerase buffer: 1 µL, Therminator DNA Polymerase of 2000 U/ml: 0.15 µL, R6G-ddUTP: 1 µL, Fluorescein-12-ddCTP: 1 µL, probe of 20 µM: 2 µL, purified product of PCR: 5 µL, and $ddH_2O$: 4.85 µL; total volume:15 µL Conditions of the extension reaction were shown in Table 2.

TABLE 2

| Conditions of extension reaction | | |
|---|---|---|
| Reaction temperature | Reaction time | Cycle number |
| 95° C. | 3 minutes | |
| 95° C. | 20 seconds | 40 |
| 51° C. | 30 seconds | |
| 72° C. | 30 seconds | |
| 72° C. | 5 minutes | |
| 16° C. | ∞ | |

(5) Correction of Fluorescence Quenching Value and Calculation of Quenching Ratio On the real-time fluorescent quantitative PCR instrument, changes of fluorescence caused by the extension reaction were detected. Original fluorescence spectra were shown in FIGS. 1~5. Channel A of the real-time fluorescent quantitative PCR instrument represented base C marked with Fluorescein-12, wherein $\lambda_{ex}$ was set to 494 nm, and $k_{em}$ was set to 517 nm. Channel B of the real-time fluorescent quantitative PCR instrument represented base T marked with R6G, wherein $\lambda_{ex}$ was set to 520 nm, and $\lambda_{em}$ was set to 548 nm.

Figure 4:
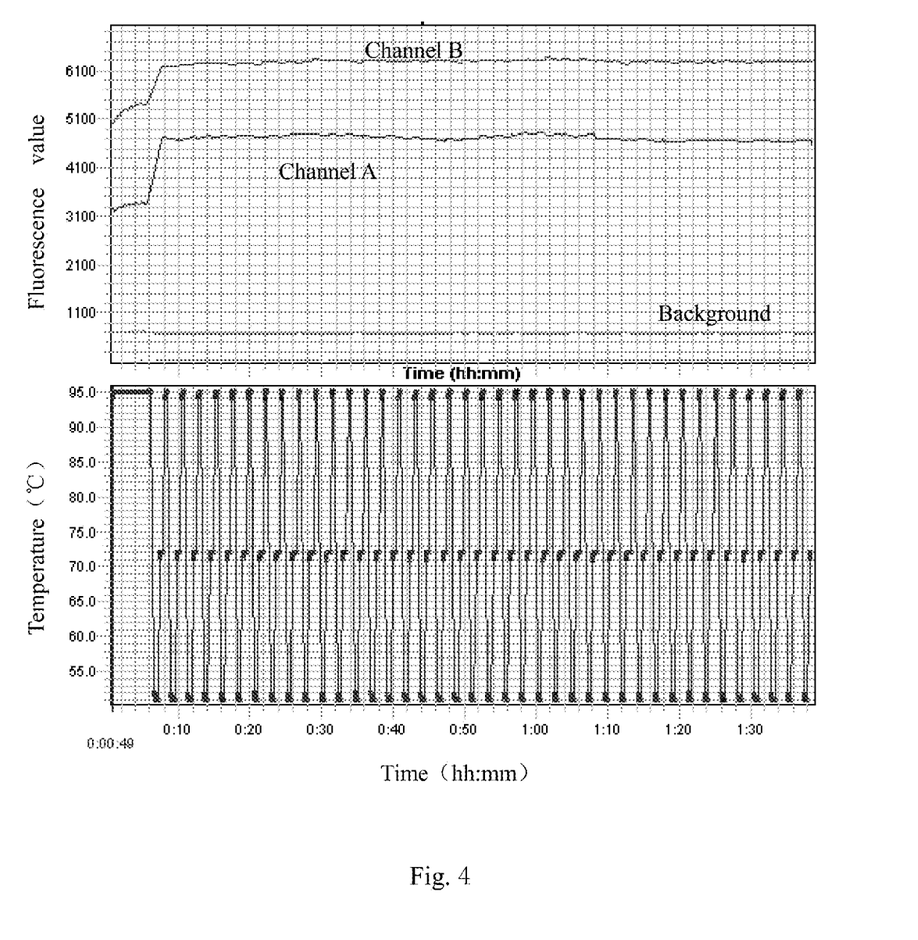
FIG. 4 is a real-time original fluorescence spectrum of an external standard control group in example 1.
Figure 5:
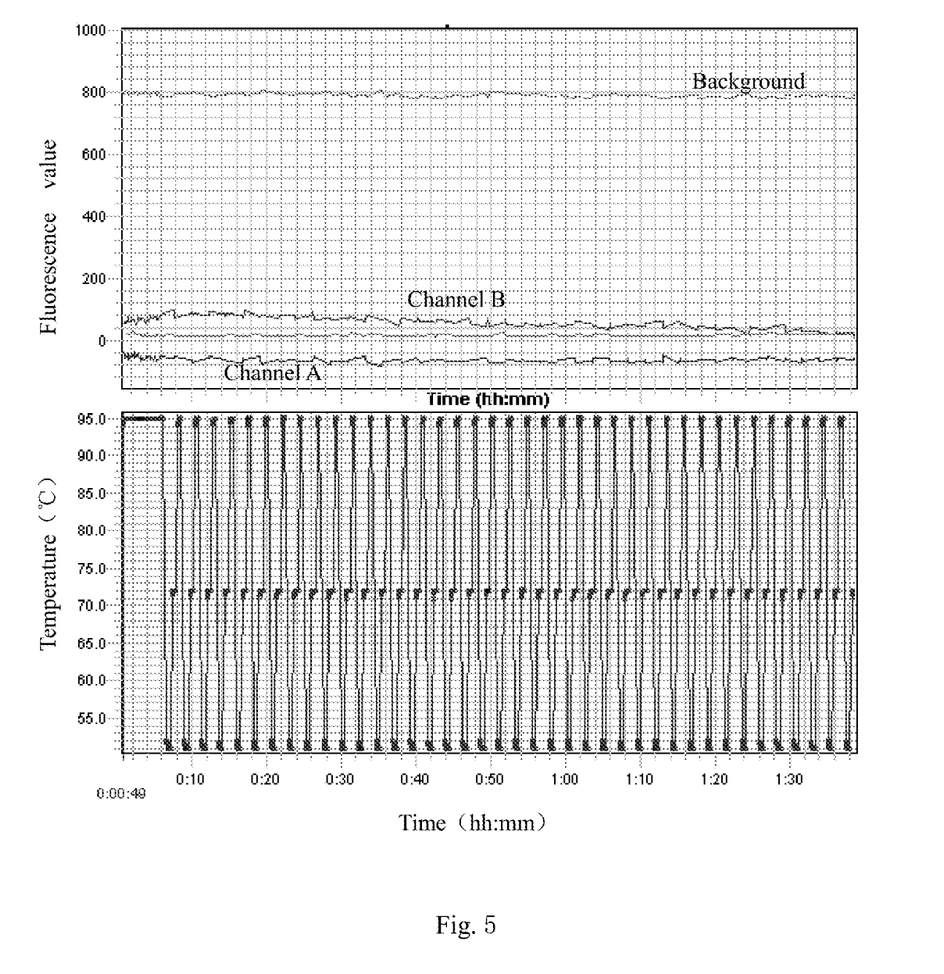
FIG. 5 is a real-time original fluorescence spectrum of a blank control group in example 1.
Figure 6:
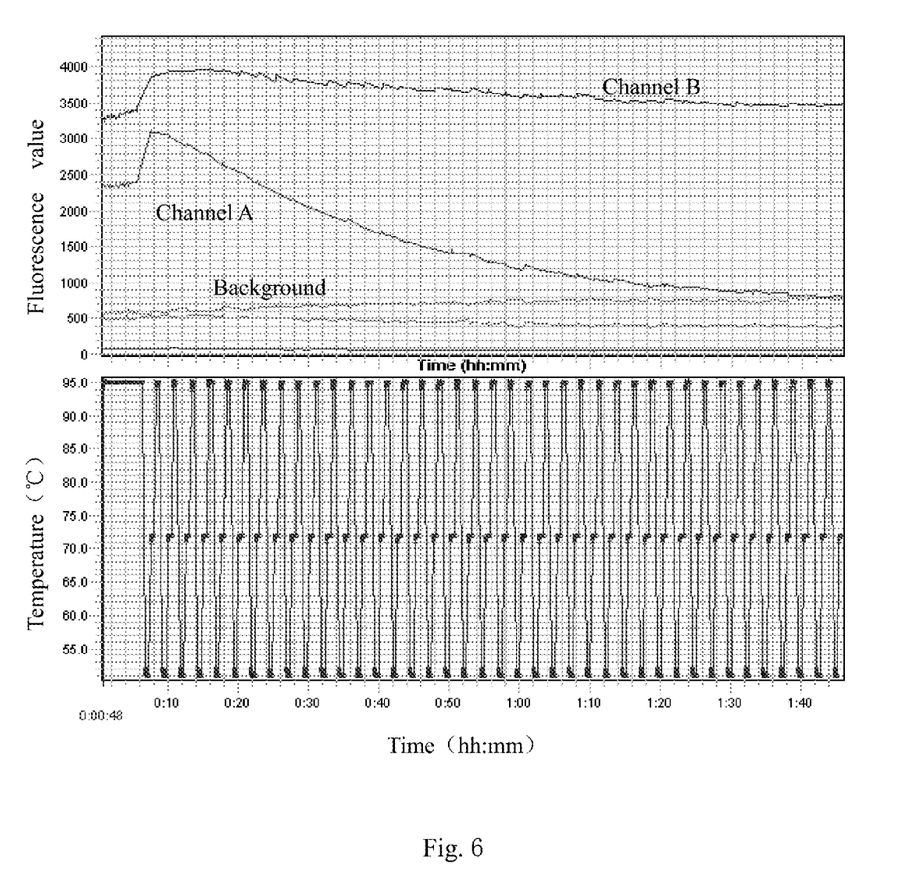
FIG. 6 is a real-time original fluorescence spectrum of experimental group 1 in example 2.
Figure 7:
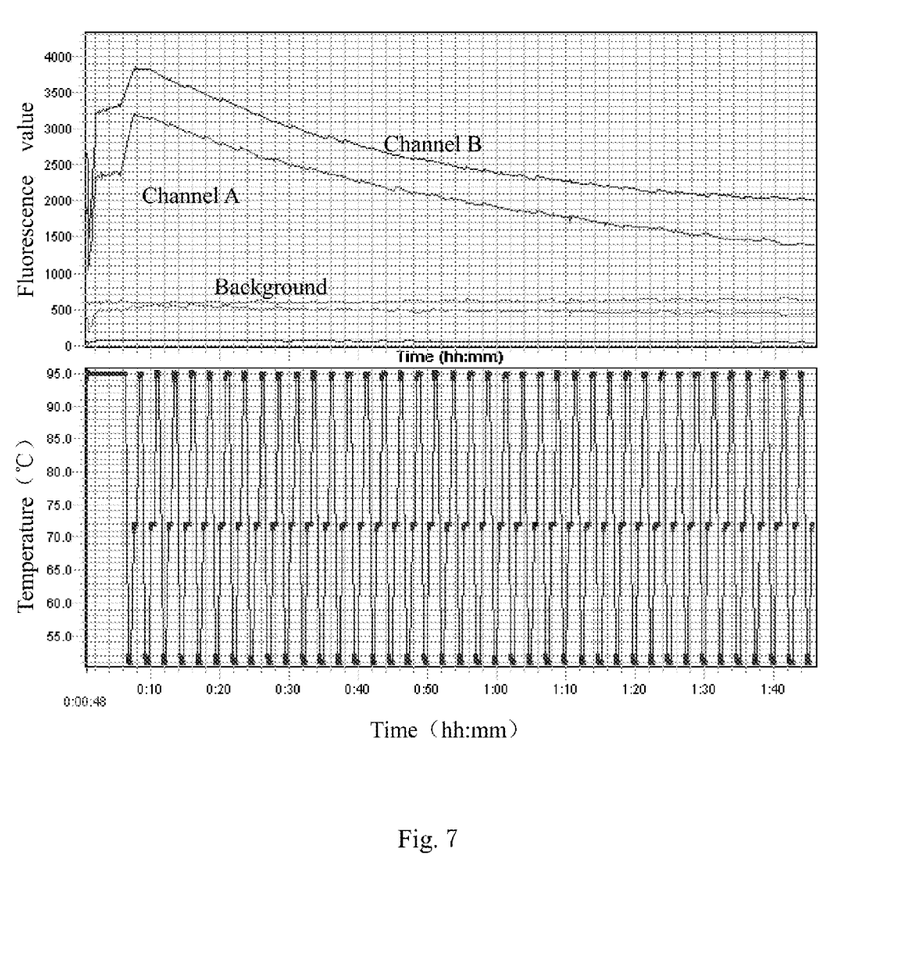
FIG. 7 is a real-time original fluorescence spectrum of experimental group 2 in example 2.
Figure 8:
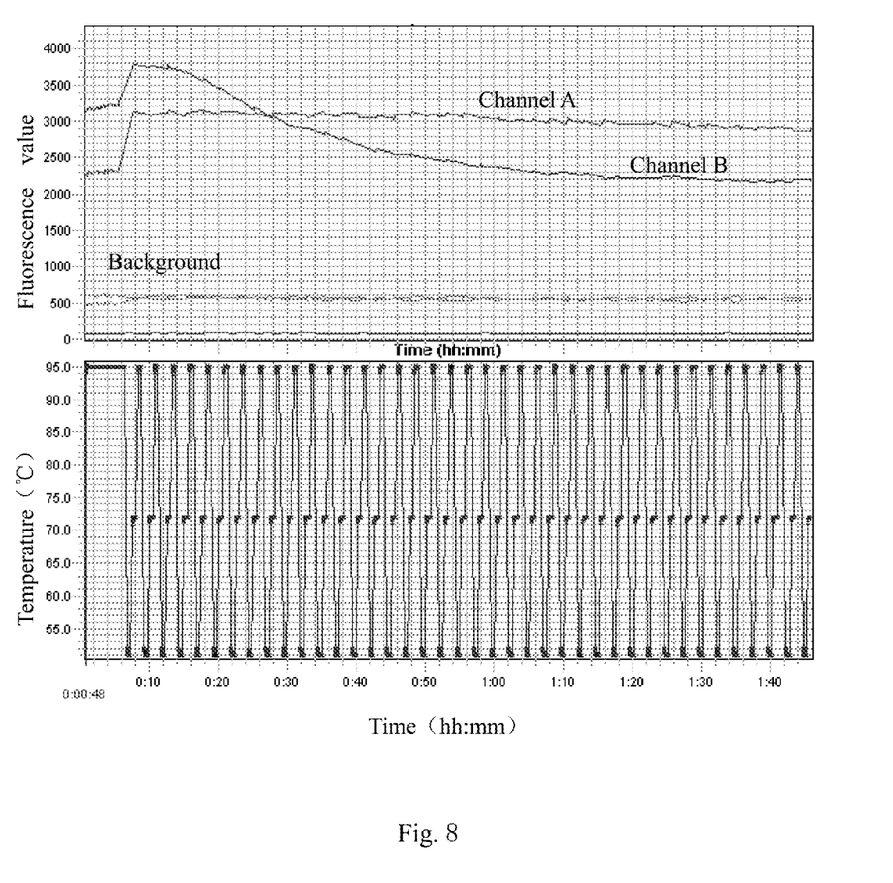
FIG. 8 is a real-time original fluorescence spectrum of experimental group 3 in example 2.
Figure 9:
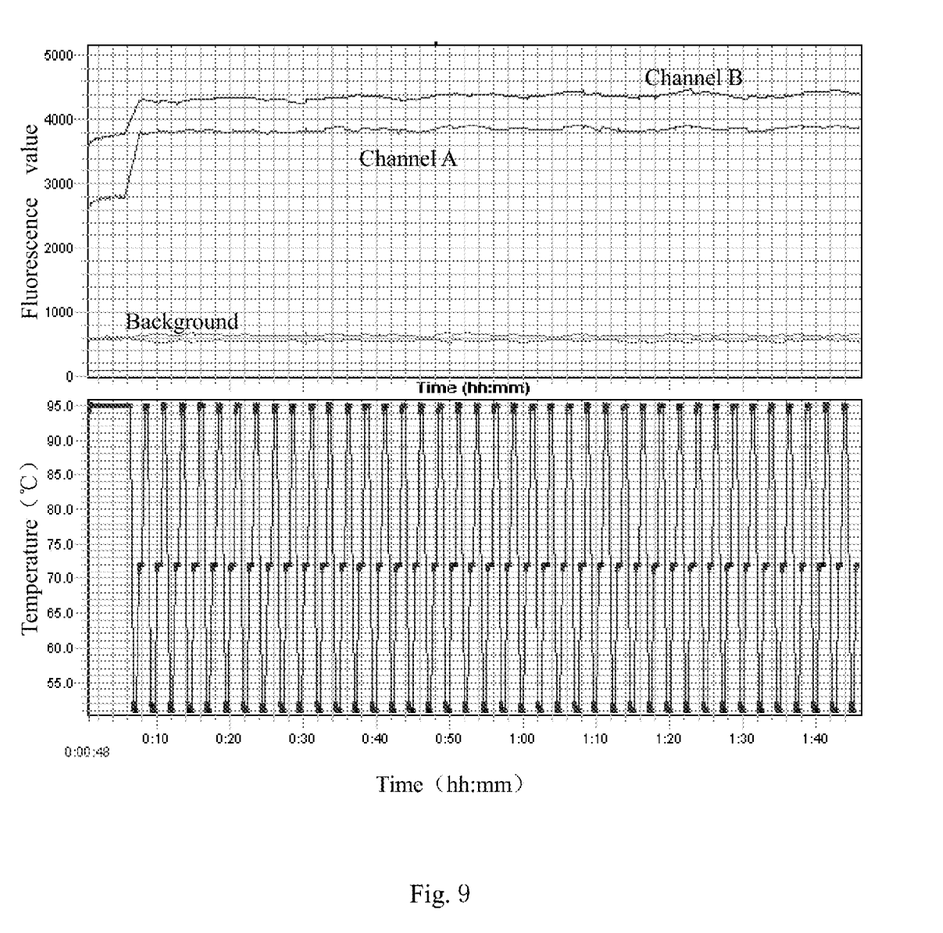
FIG. 9 is a real-time original fluorescence spectrum of an external standard control group in example 2.
Figure 10:
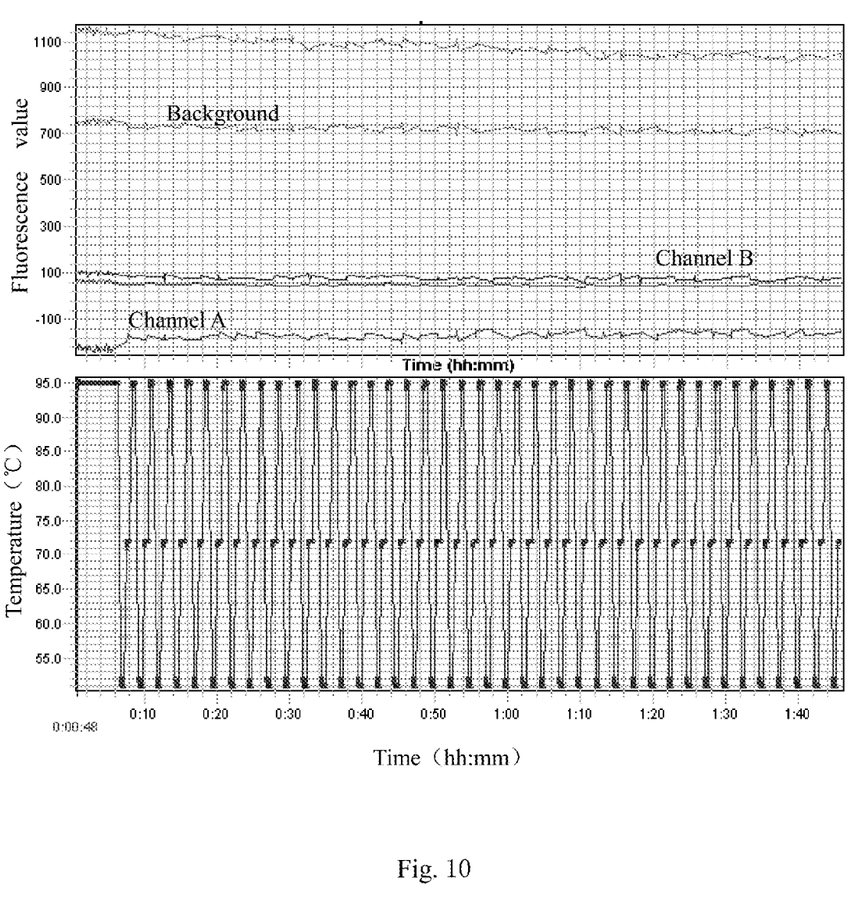
FIG. 10 is a real-time original fluorescence spectrum of a blank control group in example 2.

For the control groups, initial fluorescence values $A_{c0}$, $B_{c0}$ of channels A, B of the real-time fluorescent quantitative PCR instrument were respectively detected, and then fluorescence attenuation values (natural attenuation) $\Delta A_c$, $\Delta B_c$ after extension reaction were respectively detected. Fluorescence attenuation ratios $R_a$, $R_b$ of the channels A, B were calculated.

The fluorescence attenuation ratio of the channel A was calculated by: $R_a = \Delta A_c / A_{c0}$.

The fluorescence attenuation ratio of the channel B was calculated by: $R_b = \Delta B_c / B_{c0}$.

Figure 1:
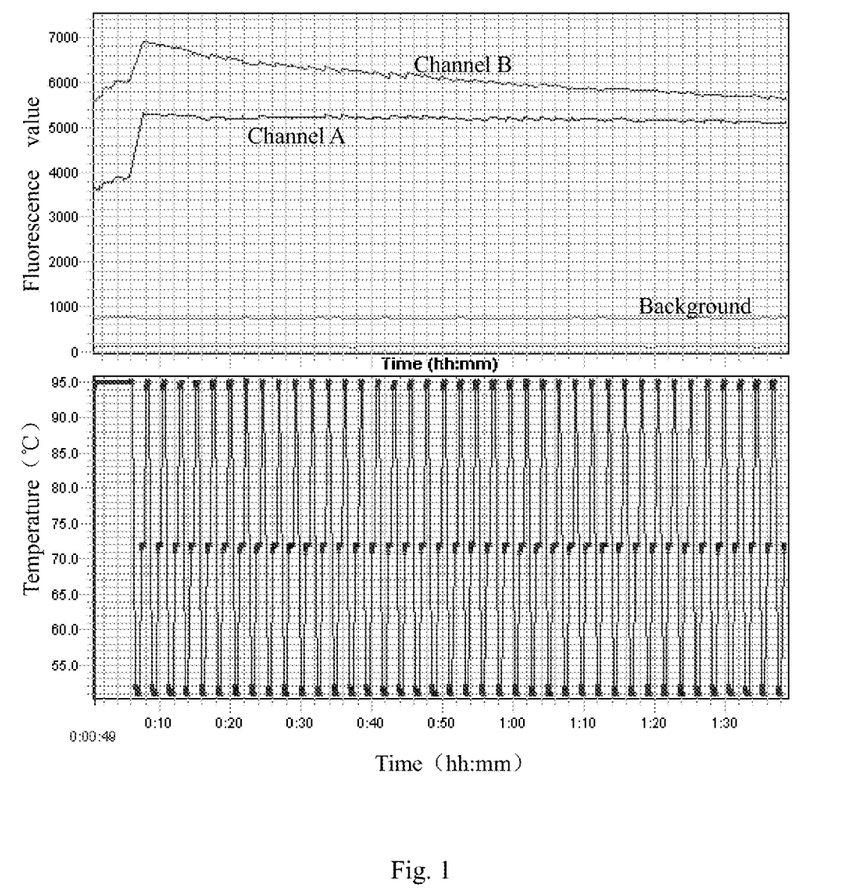
FIG. 1 is a real-time original fluorescence spectrum of experimental group 1 in example 1.
Figure 2:
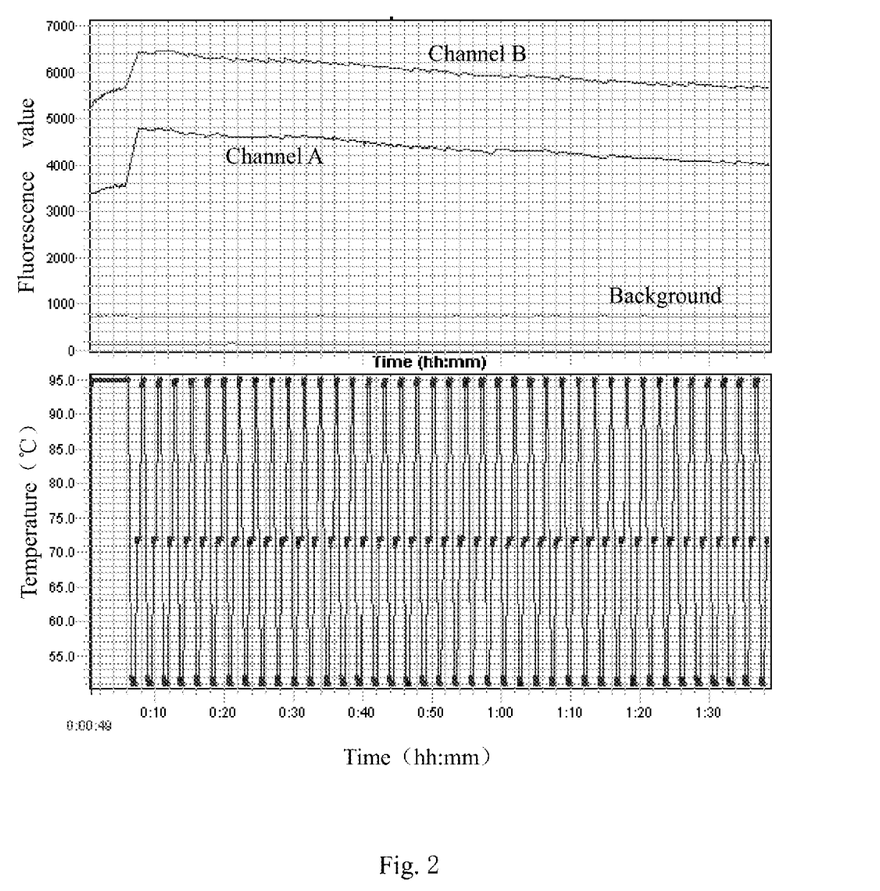
FIG. 2 is a real-time original fluorescence spectrum of experimental group 2 in example 1.
Figure 3:
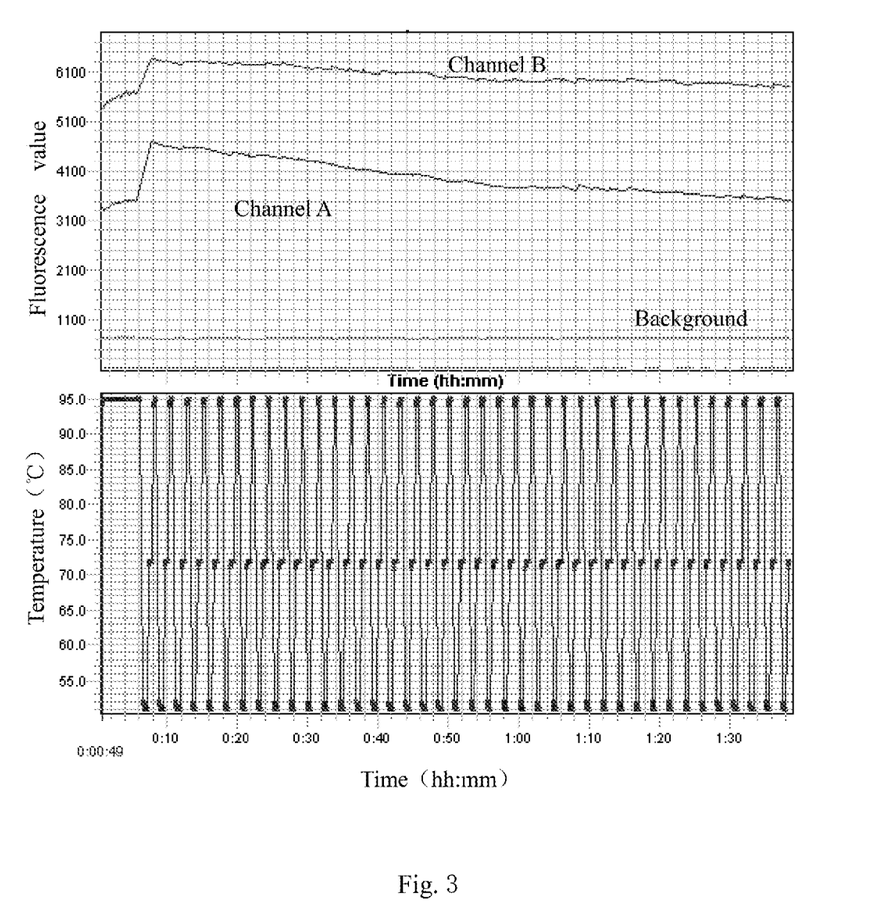
FIG. 3 is a real-time original fluorescence spectrum of experimental group 3 in example 1.

For the experimental groups, initial fluorescence values $A_{r0}$, $B_{r0}$ of channels A, B of the real-time fluorescent quantitative PCR instrument were respectively detected, and then fluorescence quenching values $\Delta A_t$, $\Delta B_t$ caused by the extension reaction were detected. Fluorescence attenuation ratios $R_a$, $R_b$ were calculated based on the above values, and the fluorescence quenching values $\Delta A_t$, $\Delta B_t$ were corrected to obtain corrected fluorescence quenching values $Q_a$, $Q_b$.

The corrected fluorescence quenching value of the channel A is calculated by: $Q_a = \Delta A_t^* (1 - R_a)$.

The corrected fluorescence quenching value of the channel B is calculated by: $Q_b = \Delta B_t^* (1 - R_b)$.

According to the corrected fluorescence quenching values $Q_a$, $Q_b$, fluorescence quenching ratios of the channels A, B were calculated.

The fluorescence quenching ratio of the channel A was calculated by: $r_a = Q_a / A_{r0}$.

The fluorescence quenching ratio of the channel B was calculated by: $r_b = Q_b / B_{r0}$.

Calculating results, represented as average value±standard deviation, were shown in Table 3.

TABLE 3

Fluorescence quenching ratios of channels A, B of 5HT2A gene in various experimental groups

| Experimental group number | Fluorescence quenching ratio of channel A | Fluorescence quenching ratio of channel B |
|---|---|---|
| 1 | 4.41% ± 1.65% | 23.01% ± 2.36% |
| 2 | 18.74% ± 0.88% | 16.38% ± 1.21% |
| 3 | 28.53% ± 0.35% | 8.23% ± 1.09% |

(6) Determination of Genotype of SNP Located in 5HT2A

Quenching determining coefficients of the channels A, B of the real-time fluorescent quantitative PCR instrument were respectively calculated, wherein the channel A represented base C marked with Fluorescein-12, and the channel B represented base T marked with R6G, and then a type of a base extending at 3' end of the probe was determined according to the quenching determining coefficient.

The quenching determining coefficient of the channel A was calculated by: $\beta_a = r_a / (r_a + r_b)$.

The quenching determining coefficient of the channel B was calculated by: $\beta_b = r_b / (r_a + r_b)$.

A larger quenching determining coefficient represented a more obvious fluorescence quenching, which meant that the gene being tested had a marker gene (A, T, C, G) at a corresponding site.

In the example 1, if $\beta \geq 65\%$, the type of the base is homozygote; if $35\% < \beta < 65\%$, the type of the base is heterozygote. The quenching determining coefficients and genotypes of various experimental groups were shown in table 4.

TABLE 4

Quenching determining coefficients and genotypes of 5HT2A gene in various experimental groups

| Experimental group number | Quenching determining coefficient of channel A | Quenching determining coefficient of channel B | Genotype |
|---|---|---|---|
| 1 | 16.09% | 83.91% | TT |
| 2 | 53.35% | 46.65% | TC |
| 3 | 77.62% | 22.38% | CC |

The genotypes of 5HT2A gene determined as above were in full accord with genotypes determined by Sanger's sequencing.

Example 2

SNP Detection of COMT with a Single Probe (1) Extracting DNA from a Sample

A proper amount of human oral mucosal epithelial cells were taken, which were provided by volunteers, and DNA was extracted from the human oral mucosal epithelial cells.

(2) PCR Amplification

Based on the DNA extracted, a COMT segment in the DNA was amplified by PCR.

Sequences of primers used in the PCR were as follows.

```
                                         (SEQ ID NO: 4)
Forward primer: GGGCCTACTGTGGCTACTCA (SEQ ID NO: 5)
Reverse primer: CCCTTTTTCCAGGTCTGACA
```

The primers recited above were provided by Shanghai Sangon Biological Engineering Co. Ltd.

A system and conditions of the PCR were same as the example 1.

(3) Purification of PCR Products

Product of the PCR was collected and then purified.

A system and conditions of purifying reaction was same as the example 1.

(4) Extension Reaction and Quenching Reaction

On a real-time fluorescent quantitative PCR instrument, a proper amount of the product of the PCR which had been purified was used as a template to perform an extension reaction with probes carrying quenching molecules and ddNTP marked with fluorescent molecules, and then oligonucleotide carrying fluorescence was obtained; meanwhile, a fluorescence quenching reaction was performed; wherein three experiments were conducted in parallel; and an external standard control group and a blank control group were set.

A sequence of the probe in the example 2 was as follows.

(SEQ ID NO: 6)
5'-TCAGGCATGCACACCTTGT(BHQ1)CCTTCA-3'

The probe was synthesized by Shuoshi Biological Technology co. Ltd.

A system and conditions of the extension reaction were same as the example 1.

(5) Correction of Fluorescence Quenching Value and Calculation of Quenching Ratio On the real-time fluorescent quantitative PCR instrument, changes of fluorescence caused by the extension reaction were detected. Original fluorescence spectra were shown in FIGS. 6-10. Channel A of the real-time fluorescent quantitative PCR instrument represented base C marked with Fluorescein-12, wherein $\lambda_{ex}$ was set to 494 nm, and $\lambda_{em}$ was set to 517 nm. Channel B of the real-time fluorescent quantitative PCR instrument represented base T marked with R6G, wherein $\lambda_{ex}$ was set to 520 nm, and $\lambda_{em}$ was set to 548 nm.

Methods for correcting the fluorescence quenching value and calculating the fluorescence quenching ratio were same as the example 1.

Calculating results, represented as average value±standard deviation, were shown in Table 5.

TABLE 5

Fluorescence quenching ratios of channels A, B of COMT in various experimental groups (single probe)

| Experimental group number | Fluorescence quenching ratio of channel A | Fluorescence quenching ratio of channel B |
|---|---|---|
| 1 | 110.36% ± 1.94% | 15.08% ± 15.10% |
| 2 | 71.03% ± 12.63% | 56.66% ± 16.12% |
| 3 | −1.47% ± 1.91% | 51.59% ± 1.58% |

(6) Determination of Genotype of SNP Located in COMT

Quenching determining coefficients of the channels A, B of the real-time fluorescent quantitative PCR instrument were respectively calculated, wherein the channel A represented base C marked with Fluorescein-12, and the channel B represented base T marked with R6G, and then a type of a base extending at 3' end of the probe was determined according to the quenching determining coefficient. Methods for calculating the quenching determining coefficient and determining the type of the base were same as the example 1.

The quenching determining coefficients and genotypes of various experimental groups were shown in table 6.

TABLE 6

Quenching determining coefficients and genotypes of COMT in various experimental groups (single probe)

| Experimental group number | Quenching determining coefficient of channel A | Quenching determining coefficient of channel B | Genotype |
|---|---|---|---|
| 1 | 87.97% | 12.03% | GG |
| 2 | 55.63% | 44.37% | GA |
| 3 | −2.92% | 102.92% | AA |

The genotypes of COMT determined as above were in full accord with genotypes determined by Sanger's sequencing.

Example 3

SNP Detection of COMT with Double Probes (1) Extracting DNA from a Sample

Same as the example 2.

(2) PCR Amplification

Same as the example 2.

(3) Purification of PCR Products

Same as the example 2.

(4) Extension Reaction and Quenching Reaction

On a real-time fluorescent quantitative PCR instrument, a proper amount of the product of the PCR which had been purified was used as a template to perform an extension reaction with two probes carrying fluorescence molecules FAM, VIC, and ddNTP carrying a quenching molecule TAMAR, and then oligonucleotide carrying fluorescence was obtained; meanwhile, a fluorescence quenching reaction was performed; wherein three experiments were conducted in parallel, and an external standard control group and a blank control group were set.

Sequences of the two probes in the example 3 were as follows.

Probe 1: 5'-TCAGGCATGCACACC (FAM) TTGTCCT-TCAC-3' (SEQ ID NO:7); wherein the probe 1 was a reverse probe, which comprises a complementary base C of a mutational site G.

Probe 2: 5'-TCAGGCATGCACACC(VIC)TTGTCCT-TCAT-3' (SEQ ID NO:8); wherein the probe 2 was a reverse probe, which comprises a complementary base T of a mutational site A.

The two probes were synthesized by Shuoshi Biological Technology co. Ltd.

A system of the extension reaction is as follows. 10× Terminator DNA Polymerase buffer: 2.5 µL, Terminator DNA Polymerase of 2000 U/ml: 0.2 µL, TAMRA-ddGTP: 5 µL, probe 1 of 20 µM: 0.5 µL, probe 2 of 20 µM: 0.5 µL, purified product of PCR: 5 µL, ddH$_2$O: 11.3 µL, total volume: 25 µL Conditions of the extension reaction was same as the example 1, as shown in Table 2.

Figure 11:
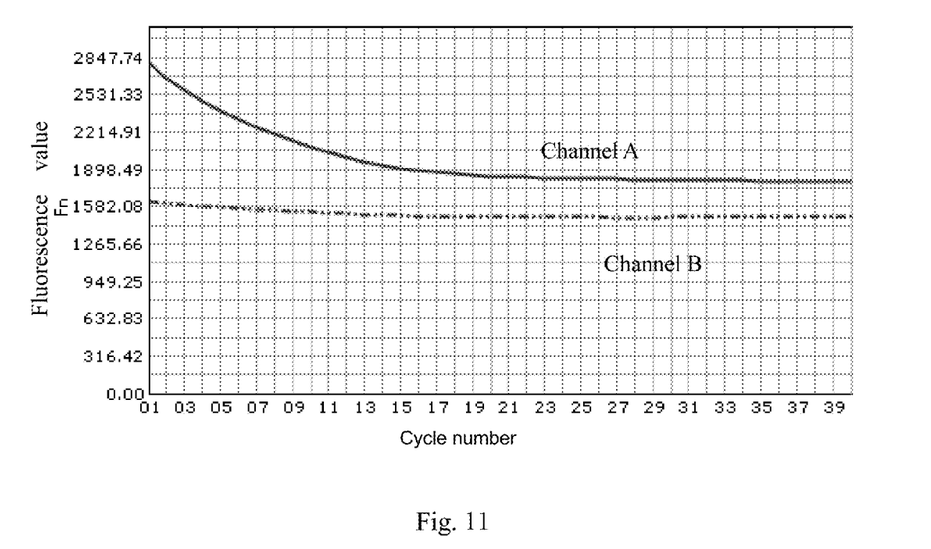
FIG. 11 is a real-time original fluorescence spectrum of experimental group 1 in example 3.
Figure 12:
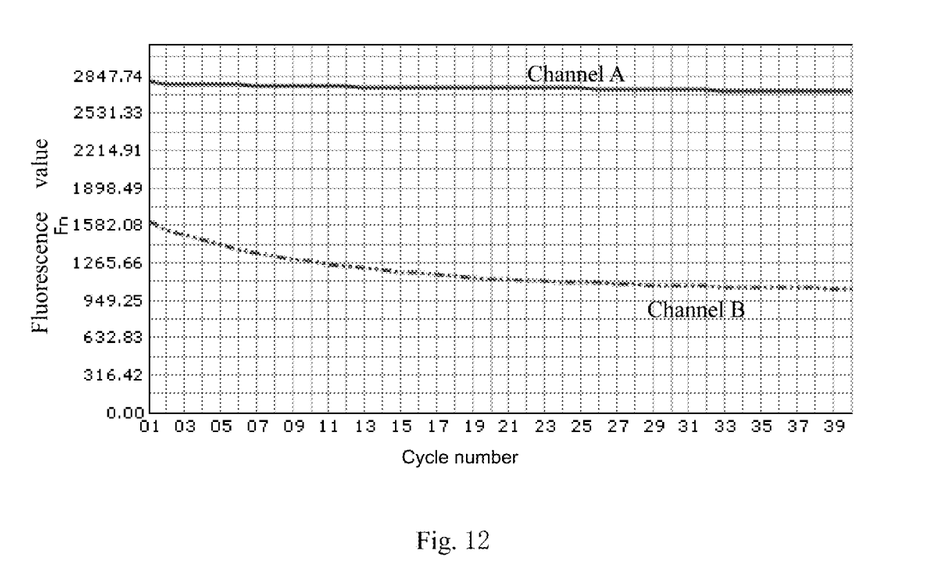
FIG. 12 is a real-time original fluorescence spectrum of experimental group 2 in example 3.
Figure 13:
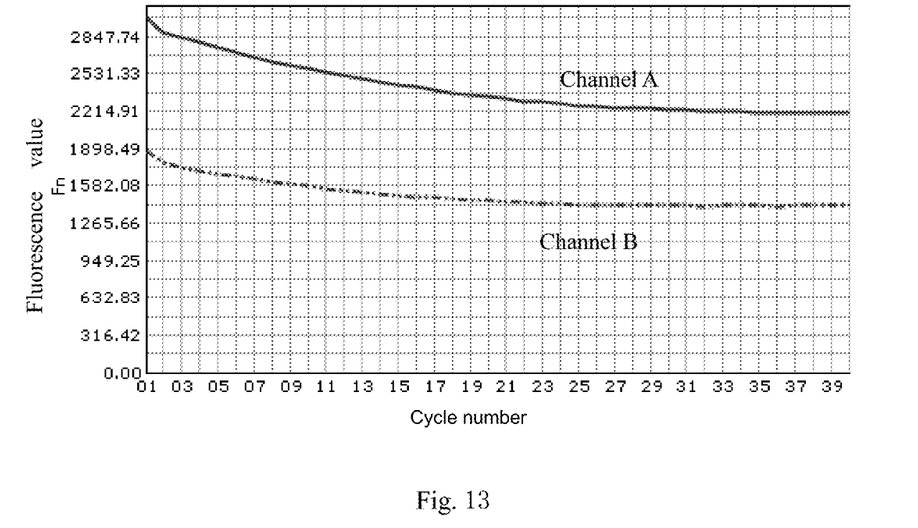
FIG. 13 is a real-time original fluorescence spectrum of experimental group 3 in example 3.
Figure 14:
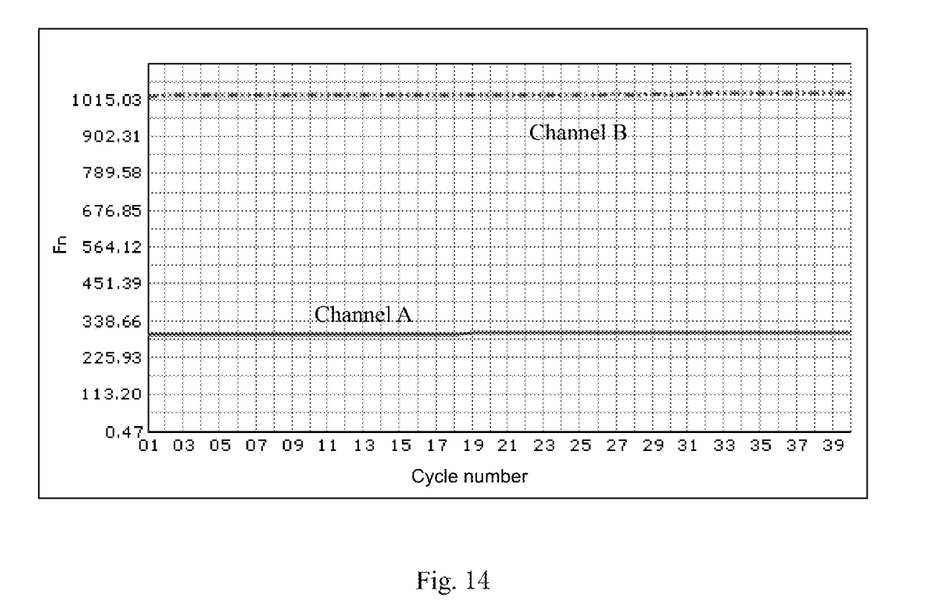
FIG. 14 is a real-time original fluorescence spectrum of an external standard control group in example 3.
Figure 15:
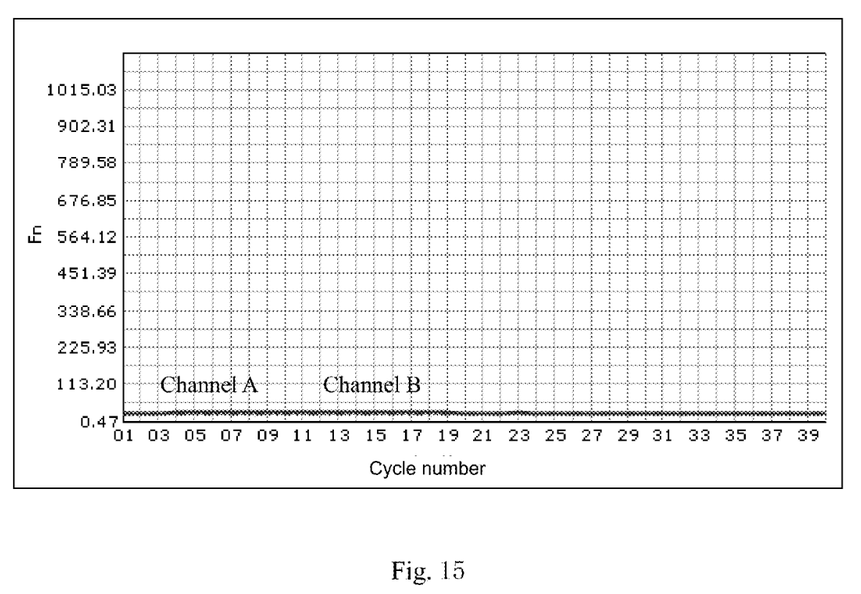
FIG. 15 is a real-time original fluorescence spectrum of a blank control group in example 3.

(5) Correction of Fluorescence Quenching Value and Calculation of Quenching Ratio On the real-time fluorescent quantitative PCR instrument, changes of fluorescence caused by the extension reaction were detected. Original fluorescence spectra were shown in FIGS. 11~13. Channel A of the real-time fluorescent quantitative PCR instrument represented the probe 1 carrying base C and marked with FAM, wherein $\lambda_{ex}$ was set to 494 nm, and $\lambda_{em}$ was set to 517 nm. Channel B of the real-time fluorescent quantitative PCR instrument represented the probe 2 carrying base T and marked with VIC, wherein $\lambda_{ex}$ was set to 520 nm, and $\lambda_{em}$ was set to 548 nm.

Methods for correcting the fluorescence quenching value and calculating the fluorescence quenching ratio were same as the example 1.

Calculating results, represented as average value±standard deviation, were shown in Table 7.

TABLE 7

Fluorescence quenching ratios of channels A, B of COMT in various experimental groups (double probes)

| Experimental group number | Fluorescence quenching ratio of channel A | Fluorescence quenching ratio of channel B |
|---|---|---|
| 1 | 35.91% ± 0.72% | 7.20% ± 1.44% |
| 2 | 3.28% ± 0.99% | 35.16% ± 1.23% |
| 3 | 26.8% ± 0.74% | 22.05% ± 3.83% |

TABLE 8

Quenching determining coefficients and genotypes of COMT in various experimental groups (double probes)

| Experimental group number | Quenching determining coefficient of channel A | Quenching determining coefficient of channel B | Genotype |
|---|---|---|---|
| 1 | 83.38% | 16.62% | GG |
| 2 | 8.55% | 91.45% | AA |
| 3 | 55.07% | 44.93% | GA |

(6) Determination of Genotype of SNP Located in COMT

Quenching determining coefficients of the channels A, B of the real-time fluorescent quantitative PCR instrument were respectively calculated, wherein the channel A represented base C marked with FAM, and the channel B represented base T marked with VIC, and then a type of a base extending at 3' end of the probe was determined according to the quenching determining coefficient. Methods for calculating the quenching determining coefficient and determining the type of the base were same as the example 1.

The quenching determining coefficients and genotypes of various experimental groups were shown in table 8.

The genotypes of COMT determined as above were in full accord with genotypes determined by Sanger's sequencing.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. The oligonucleotide probe, comprising 15-45 nucleotides and marked with a quenching molecule (BHQ1, BHQ2, BHQ3, TAMRA, or Dabcyl or Eclipse); a distance between said quenching molecule and 3' end of said oligonucleotide sequence marked with said fluorescence molecule (R6G, Cy3, Cy5, or FAM) is 3-35 bp, wherein said oligonucleotide probe comprises a single probe having a sequence as SEQ ID NO:3 or SEQ ID NO:6.

2. The oligonucleotide probe, comprising 15-45 nucleotides and marked with a fluorescence molecule (R6G, Cy3, Cy5, or FAM); a distance between said fluorescence molecule and 3' end of said oligonucleotide sequence marked with said quenching molecule (BHQ1, BHQ2, BHQ3, TAMRA, or Dabcyl) is 3-35 bp, wherein said oligonucleotide probe comprises double probes respectively having sequences as SEQ ID NO:7 or SEQ ID NO:8.

* * * * *